United States Patent [19]

Weil

[11] 4,154,966

[45] May 15, 1979

[54] PROCESS FOR THE PREPARATION OF DIBROMONEOPENTYLGLYCOL (DBNG)

[75] Inventor: Theodor Weil, Beer Sheva, Israel

[73] Assignee: Dead Sea Bromine Co. Ltd., Beer Sheva, Israel

[21] Appl. No.: 854,377

[22] Filed: Nov. 23, 1977

[51] Int. Cl.$^2$ ............................................. C07C 31/34
[52] U.S. Cl. ................................................... 568/844
[58] Field of Search ............................... 568/841, 844

[56] References Cited

U.S. PATENT DOCUMENTS

| | | | |
|---|---|---|---|
| 3,876,509 | 4/1975 | Davis et al. ........................... | 568/844 |
| 3,883,581 | 5/1975 | Davis et al. ........................... | 568/844 |
| 3,932,541 | 1/1976 | Davis et al. ........................... | 568/844 |

*Primary Examiner*—Howard T. Mars

*Attorney, Agent, or Firm*—Robert J. Koch

[57] ABSTRACT

The present invention relates to a process for the preparation of 2,2-bis-(bromomethyl)-1,3-propanediol comprising reacting pentaerythritol with HBr in the presence of 0.5–4% calculated on the weight of said pentaerythritol of a catalyst selected among the group comprising carboxylic acids, their anhydrides and esters, in an inert solvent being selected from the group comprising aromatic hydrocarbons and aromatic and aliphatic halohydrocarbons having a boiling point between 80–145° C., removing the water simultaneously in the form of a HBr solution, and thereafter adding a neutralizing agent.

2,2-bis-(bromomethyl)-1,3-propanediol is utilized as reactive component in fire retardant polyesters and polyurethanes.

13 Claims, No Drawings

PROCESS FOR THE PREPARATION OF DIBROMONEOPENTYLGLYCOL (DBNG)

The present invention relates to a process for the preparation of dibromoneopentylglycol being 2,2-bis-(bromomethyl)-1,3-propanediol (also referred to as "DBNG").

2,2-bis-(bromomethyl)-1,3-propanediol is an important compound which is used as a reactive component in fire retardant polyesters and polyurethanes.

However, so far it has been very difficult to obtain pure 2,2-bis-(bromomethyl)-1,3-propanediol as usually it has been obtained in admixture with tribromoneopentylalcohols being 2,2-bis (Bromomethyl)-3-bromo-propanediol and other brominated pentaerythritols. There exist certain processes to separate both compounds from each other. However, these processes are quite complicated and cumbersome.

U.S. Pat. No. 3,932,541 which describes also many of the previous methods known for preparing brominated pentaerythitols, describes and claims a process for the preparation of brominated pentaerythitols in which pentaerythritol (also referred to as PE) is reacted with HBr in the liquid phase at a temperature of from about 85° to about 135° C. in a solvent selected from the groups consisting of benzene, toluene, xylene, a saturated hydrocarbon solvent, a substantially non-reactive brominated or chlorinated hydrocarbon solvent, and water, containing as a catalyst an alkanoic acid of from 2 to 8 carbon atoms or its anhydride having a concentration of from about 0.8 to about 25 mole percent per mole of pentaerylthritol continuously throughout the reaction to saturate the reaction mixture with HBr while retaining in the reaction mixture until completion of the reaction water formed during the reaction and any water used as solvent.

However, it is nowhere stated in said specification that by said process one can obtain pure 2,2-bis-(bromomethyl)-1,3-propanediol. On the contrary from all examples it becomes clear, that there are obtained mixtures of brominated pentaerythritols.

It has been desirable therefore to find a process by which pure 2,2-bis-(bromomethyl-1,3-propanediol which does not comprise any other brominated pentaerythritol, can be produced. This process should be quite simple and cheap and give good yields.

It has now been found that when the reaction described above is performed with continuous removal of the water very pure 2,2-bis-(bromomethyl)-1,3-propanediol is obtained in high yields.

The present invention thus consists in a process for the preparation of 2,2-bis-(bromomethyl)-1,3-propanediol comprising reacting pentaerythritol with HBr in the presence of 0.5-4%, calculated on the weight of said PE, of a catalyst selected among the group comprising carboxylic acids, their anhydrides and esters, in an inert solvent being selected from the group comprising aromatic hydrocarbons and aromatic and aliphatic halohydrocarbons having a boiling point between 80°-145° C., removing the water simultaneously in the form of a HBr solution and thereafter adding a neutralising agent.

The amount of HBr should advantageously be in slight excess above the quantity needed to form 2,2-bis-(bromomethyl)-1,3-propanediol and the quantity needed to remove the water in the form of an approximately 50% wt/wt HBr solution.

The ratio solvent pentaerythritol should advantageously be at least 1:1. However, preferably the ratio is higher, e.g. 2:1.

The process according to the present invention yields 2,2-bis-(bromomethyl)-1,3-propanediol in yields of 80-90% in a purity of 98%. This is in contradiction to the results obtained by Example 3 of U.S. Pat. No. 3,932,541.

The main differences which may explain the different results between both processes are the following:

a. In the process according to the present invention the final reaction mixture is neutralised. Whereas no such neutralisation is performed in said Example 3.
b. In Example 3 all liquids, i.e., the solvent, water and excess HBr are stripped off after the reaction has been terminated. No such step is performed in the process according to the present invention; no stripping off is performed and on the contrary the solvent serves as crystallizing agent.

The neutralising agent may be chosen among any suitable bases, e.g. $NaHCO_3$. Moreover, the reaction is preferably performed with exclusion of oxygen, e.g. under a nitrogen atmosphere, in particular in case that toluene or xylene is used as solvent.

The catalyst utilised is preferably acetic acid or its anhydride in an amount of 2-3%. However, other catalysts also, e.g. caprylic acid and Lauric acid have given good results. As solvent there are preferred toluene, o,m,p-xylene or their mixtures, and chlorobenzene.

The present invention will now be illustrated with reference to the following examples without being limited by them. All temperatures are given in degrees centigrade.

EXAMPLE 1

Into a 3-necked flask equipped with dip-pipe for HBr addition, stirrer, Dean-Stark azeotropic water separator, were placed.

100 g commercial grade "Monopentaerythritol"
2.5 ml acetic acid; and
100 ml toluene Under vigourous stirring HBr gas was added to the mixture as fast as possible at 100°. After 1 hour at that temperature heating was increased until intensive reflux started. Aqueous (approx. 50%) HBr was collected in the Dean Stark adaptor at quite constant rate until 42 ml had accumulated. Excess HBr gas was collected by absorption in water at the exit of the apparatus. HBr addition was stopped and the mixture heated for half hour to drive out the excess HBr. The mixture was cooled to about 80° and then neutralised with a saturated aqueous $NaHCO_3$ solution. On further cooling 2,2-bis-(bromomethyl)-1,3-propanediol precipitated. At 20° the mixture was filtered and the 2,2-bis-(bromomethyl)-1,3-propanediol obtained washed with ice-water on the filter. The solid was sucked dry and then dried in vacuo at 80°. This example was repeated a number of times. The yields were between 80 and 90%; the purity was 98%; mp 109–110.

When the experiment was performed under a nitrogen atmosphere the reaction mixture obtained was colourless, whereas otherwise the slight colour disappeared after the neutralisation step.

EXAMPLE 2

In a 500 ml 3-necked flask fitted with a dip-pipe, stirrer and a Dean-Stark adaptor for azeotropic water removal 100 g of pentaerythritol, 2.5 ml of acetic acid and 120 ml of chlorobenzene were heated to just below reflux temperature and approximately 200 g of HBr gas was added as fast as it was absorbed.

After one hour, when all the solid had disappeared the temperature was raised in reflux. After 4½ hours 35 ml of aqueous HBr had been collected in the Dean Stark adaptor and the HBr addition was interrupted. The apparatus was flushed with air to drive out excess HBr and, after cooling to 90° the remaining acid was neutralized by addition of aqueous $NaHCO_3$. The neutral solution was cooled to 10° and the precipitated product filtered off, washed with 50 ml of ice-water with 20 ml of chlorobenzene and dried. 150 g of 2,2-bis-(bromomethyl)-1,3-propanediol, m.p. 109°–110° were obtained. From the filtrate the organic phase was isolated and used without further treatment for a subsequent batch, in which 100 g of pentaerythritol was used, but no additional catalyst and from which 165 g of 2,2-bis-(bromomethyl)-1,3-propanediol, m.p. 109°–110° were isolated.

EXAMPLE 3

The procedure described in Example 1 was repeated replacing the acetic acid by 10 g of caprylic acid to yield 158 g of 2,2-bis-(bromomethyl)-1,3-propanediol.

EXAMPLE 4

The procedure described in Example 1 was repeated replacing toluene by xylene (a commercial mixture containing o-,m-,p-xylene and ethylbenzene) as solvent. 160 g of 2,2-bis-(bromomethyl)-1,3-propanediol, m.p. 108°–110° was obtained. The product was, however, purple coloured and the xylene recovered from the filtrate was brown.

EXAMPLE 5

The procedure described in Example 4 was repeated under exclusion of oxygen by flushing the apparatus with nitrogen. 168 of 2,2-bis-(bromomethyl)-1,3-propanediol m.p. 108°–110° was obtained. The product was perfectly white and the xylene recovered was only very slightly coloured.

EXAMPLE 6

The procedure descibed in Example 5 was repeated using as catalyst acetic acid anhydride. There was also received 168 g of white 2,2-bis-(bromomethyl)-1,3-propanediol, m.p. 108°–110°.

I claim:

1. In a process for preparing 2,2-bis-(bromomethyl)-1,3-propanediol comprising brominating pentaerythritol by reacting it with HBr in a reaction mixture comprising a catalyst selected from the group consisting of carboxylic acid, carboxylic acid anhydrides and carboxylic acid esters, in an inert solvent selected from the group consisting of aromatic hydrocarbons and aromatic and aliphatic halohydrocarbons the improvement comprising (a) reacting gaseous HBr with said pentaerythritol in the presence of 0.5 to 4% of said catalyst, based on the weight of pentaerythritol, wherein said solvent has a boiling point of between 80° and 145° C., and whereby water is formed in the reaction mixture;

(b) azeotropically removing the water in the form of an aqueous-HBr solution from the reaction mixture during the brominating step;

(c) neutralizing the reaction mixture subsequently to the brominating step;

(d) cooling the neutralized reaction mixture sufficiently to precipitate 2,2-bis-(bromomethyl)-1,3-propanediol; and (e) recovering the precipitated 2,2-bis-(bromomethyl)-1,3-propanediol from the cooled reaction mixture.

2. The process of claim 1 wherein the neutralizing step is carried out by a sodium bicarbonate neutralizing agent.

3. The process of claim 1 wherein the reaction is carried out in an oxygen free environment.

4. The process of claim 3 wherein the reaction step is conducted in a nitrogen atmosphere.

5. The process of claim 1 wherein the amount of catalyst utilized is 2 to 3%.

6. The process of claim 1 wherein the catalyst is selected from the group consisting of acetic acid and acetic acid anhydride.

7. The process of claim 1 wherein the catalyst is caprylic acid.

8. The process of claim 1 wherein the catalyst is lauric acid.

9. The process of claim 1 wherein the solvent is toluene.

10. The process of claim 1 wherein the solvent is chlorobenzene.

11. The process of claim 1 wherein the solvent is xylene.

12. The process of claim 1 wherein the ratio of solvent to pentaerythritol is at least 1:1.

13. The process of claim 12 wherein the ratio of solvent to pentaerythritol is 2:1.

* * * * *